US00PP28016P3

(12) United States Plant Patent
Olesen

(10) Patent No.: US PP28,016 P3
(45) Date of Patent: May 16, 2017

(54) MINIATURE ROSE PLANT NAMED 'POULPAR089'

(50) Latin Name: ***Rosa* hybrid**
Varietal Denomination: Poulpar089

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/756,252

(22) Filed: Aug. 20, 2015

(65) Prior Publication Data

US 2017/0055388 P1 Feb. 23, 2017

(51) Int. Cl.
*A01H 5/02* (2006.01)

(52) U.S. Cl.
USPC ..... Plt./121

(58) Field of Classification Search
USPC ..... Plt./121
See application file for complete search history.

(56) References Cited

PUBLICATIONS

PLUTO Plant Variety Database Aug. 2, 2016. p. 1.*
Indoor Roses Main Varieties 2013 by Poulsen.*

* cited by examiner

*Primary Examiner* — Annette Para

(57) ABSTRACT

A new garden rose plant of the miniature class which has abundant, pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar089'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar089', originated as a single seedling from the stated cross.

The new variety may be distinguished from its male pollen parent and female seed parent primarily by the following characteristics. The new variety has flowers which are Red Group 65A and 65C, while the male pollen parent has flowers which are Red Group 52B. The female pollen parent has flowers which are Red-Purple Group 69A.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar089' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar089' was selected in the spring of 2008 by the inventor as a single plant from the progeny of the aforementioned hybridization.

Asexual reproduction of 'Poulpar089' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpar089' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar089'.

Specifically illustrated is open flowers, a cluster of flower buds on a bare stem, flower petals detached, juvenile growth showing anthocyanin, leaves, and reproductive flower parts. Plants shown are one year old.

DETAILED DESCRIPTION OF THE VARIETY

The following is a description of 'Poulpar089', as observed in its growth in in a field nursery in Marion County, Oreg. Observed plants are one year old, and were grown on their own roots. Color references are made using The Royal Horticultural Society (London, England) Colour Chart, 2001, except where common terms of color are used.

For a comparison, several physical characteristics of the rose variety 'Poulty010', U.S. Plant Pat. No. 24,872 are compared to 'Poulpar089' in Chart 1.

CHART 1

| | 'Poulpar089' | 'Poulty010' |
|---|---|---|
| Petal Count | 25 | 35 |
| Flower Diameter | 65 mm | 35 to 45 mm |
| General Tonality of Flower Color | Open flowers are Red-Purple Group 65A and Red-Purple Group 65C. | Red Group 33A |

Flower and Flower Bud

Blooming habit: Continuous.

Flower bud:

*Size.*—Upon opening, 25 mm in length from base of receptacle to end of bud. Bud diameter is 10 mm.

*Bud form.*—Ovoid.

*Bud color.*—As sepals divide petals are Red-Purple Group 62B.

*Sepal inner surface.*—Color: Yellow-Green Group 145A with intonations of Greyed-Purple Group 185B. Surface: Lightly pubescent.

*Sepal outer surface.*—Color: Yellow-Green Group 145A with strong intonations of Greyed-Purple Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—29 mm long, 9 mm wide.

*Receptacle.*—Texture: Smooth. Size: 5 mm in height, 9 mm wide. Color: Yellow-Green Group 144A with light intonations of Greyed-Purple Group 183B. Shape: Broad funnel.

*Pedicel.*—Surface: Smooth. Length: 35 mm. Diameter: 2 mm on average. Color: Yellow-Green Group 144A with strong intonations of Greyed-Orange Group 176A. Strength: Strong.

*Peduncle.*—Length: 2 to 11 cm. Diameter: About 3 mm. Color: Yellow-Green Group 144A with strong intonations of Greyed-Purple Group 183D. Texture: Smooth.

Flower bud development: Flower buds are borne in corymbs of 7 to 9 flower buds per stem.

Flower bloom:

*Fragrance.*—Light flora.

*Duration.*—The blooms have a duration on the plant of approximately 15 days. Petals fall cleanly away from plant after flowers have fully matured.

*Size.*—Flower diameter is 65 mm when open. Flower depth is 30 mm.

*Flower shape.*—Rosette semi double flower with many slightly overlapping petals of different sizes.

*Shape of flower, side view.*—The upper portion is flat. The lower portion is concave.

Petalage: Under normal conditions, flowers have 25 petals total, about 5 of which are petaloids.

General tonality of flower: Open flowers are Red-Purple Group 65A and Red-Purple Group 65C.

Petal color:

*Upon and after opening, outer petals.*—Upper surface: Red-Purple Group 69B with intonations of Red-Purple Group 65A. Lower surface: Red-Purple Group 65A with marginal intonations of Red-Purple Group 65C.

*Upon and after opening, inner petals.*—Upper surface: Red-Purple Group 69B with intonations of Red-Purple Group 65A. Intonations of Yellow-Orange Group 18C at the base. Lower surface: Red-Purple Group 65A with marginal intonations of Red-Purple Group 65C.

*Basal petal spots, upon and after opening.*—Upper surface: Yellow Group 4B. Lower surface: Yellow Group 4B.

Petals:

*Petal reflex.*—Somewhat reflexed.

*Margin.*—Entire and uniform. Moderate undulations.

*Shape.*—Generally rounded. Apex shape: Rounded. Base shape: Obtuse.

*Size.*—About 30 mm (l)×30 mm (w).

*Texture.*—Smooth.

*Thickness.*—Above average.

Petaloids:

*Size.*—10 mm (l) by 5 mm (w).

*Quantity.*—About 5.

*Shape.*—Acute base and rounded apex.

*Color.*—Red Group 39B with a basal petal spot of Yellow Group 4B on the upper surface. The lower surface is Red Group 39B with a basal petal spot of Yellow Group 4B.

Reproductive flower parts:

*Pollen.*—None observed.

*Anthers.*—Size: 2 mm in length. Color: Greyed-Yellow Group 160A. Quantity: 40 on average.

*Filaments.*—Color: Orange Group 29A and Yellow Group 13B. Length: 5 mm.

*Pistils.*—Length: 10 mm. Quantity: 25 on average.

*Stigmas.*—Color: Greyed-Red Group

*Styles.*—Color: Greyed-Purple Group 184A.

*Location of stigmas.*—Level in location relative to the length of the filaments and the height of the anthers.

*Hips.*—None Observed.

Plant

Plant growth: Upright, bushy. Plants are 35 cm in height, and 30 cm wide.

Stems:

*Color.*—Juvenile growth: Yellow-Green Group 144B with intonations of Greyed-Red Group 182B. Mature growth: Yellow-Green Group 144A.

*Length.*—On average, canes are 20 cm from the base of the plant to the flowering portion.

*Diameter.*—5 to 6 mm.

*Internodes.*—On mature canes about 30 mm between nodes.

*Surface texture.*—Young wood: Rough with small prickles. Older wood: Smooth.

Long prickles:

*Incidence.*—9 prickles per 10 cm of stem.

*Size.*—Average length of prickles on mature stems is 6 mm.

*Shape.*—Upper portion is linear. Lower portion is concave.

*Color*.—Juvenile prickles: Greyed-Red Group 182A. Mature prickles: Greyed-Orange Group 164B.

Plant foliage:

*Compound leaf*.—100 mm (l)×60 (w).

*Quantity*.—3 leaves per 10 cm of stem on average.

*Color of juvenile foliage*.—Upper side: Yellow-Green Group 146A. Lower side: Yellow-Green Group 146A. Anthocyanin: Strong, Greyed-Purple Group 187A throughout the leaflet.

*Color of mature foliage*.—Upper side: Yellow-Green Group 147A. Lower side: Yellow-Green Group 147B.

Plant leaves and leaflets:

*Stipules*.—Size: 12 mm long, 4 mm wide. Quantity: 2 per compound leaf. Shape: Linear, slightly broad based with outward extending apices. Margins: Finely serrated. Color: Yellow-Green Group 144B.

*Petiole*.—Length: 30 mm. Diameter: 1 mm.

*Upper surface*.—Color: Yellow-Green Group 144A.

*Lower surface*.—Color: Yellow-Green Group 144B.

*Rachis*.—Length: 40 mm. Upper surface: Color: Yellow-Green Group 144A.

*Lower surface*.—Color: Yellow-Green Group 144B.

*Leaflet*.—Quantity: Normally 5 leaflets. Margins: Serrated. Size: On average terminal leaflets are 30 mm long, 22 mm wide. Shape: Generally elliptical. Base: Rounded. Apex: Cuspidate. Texture: Smooth. Thickness: Average. Arrangement: Odd pinnate. Venation: Reticulate. Glossiness: Somewhat glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar089', substantially as illustrated and described herein, due to its abundant pink flowers, disease resistance, and extended period of bloom.

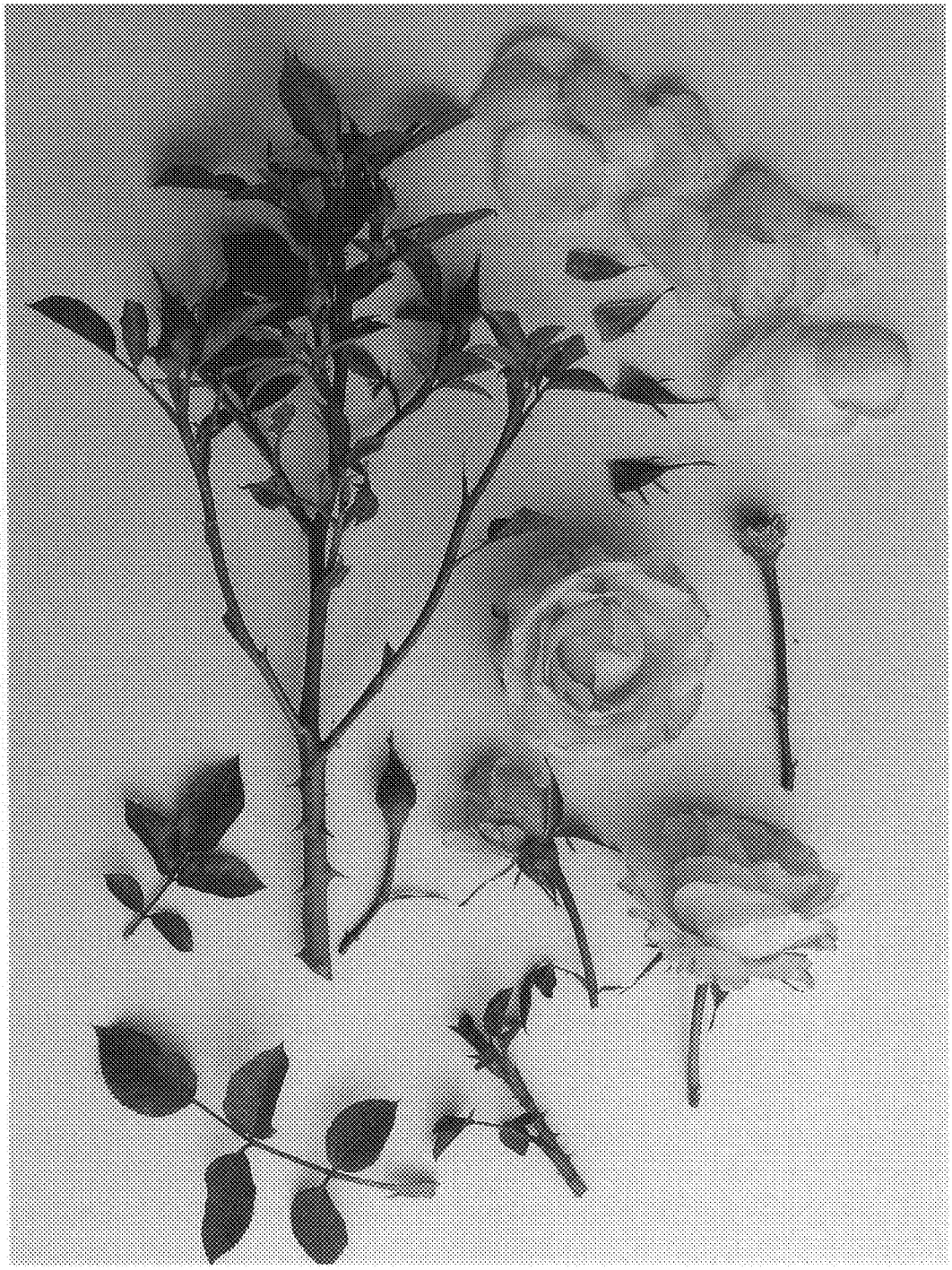

* * * * *